United States Patent
Jeffcoat et al.

(10) Patent No.: US 6,712,778 B1
(45) Date of Patent: Mar. 30, 2004

(54) IMPLANTABLE MECHANICAL FORCE SENSOR

(75) Inventors: Robert Lee Jeffcoat, Vestavia Hills, AL (US); Lance C. Ramp, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/089,693

(22) PCT Filed: Sep. 29, 2000

(86) PCT No.: PCT/US00/26891

§ 371 (c)(1), (2), (4) Date: Apr. 1, 2002

(87) PCT Pub. No.: WO01/22880

PCT Pub. Date: Apr. 5, 2001

Related U.S. Application Data

(60) Provisional application No. 60/157,189, filed on Sep. 30, 1999.

(51) Int. Cl.[7] .......................... A61B 5/103; A61B 5/117
(52) U.S. Cl. ..................................................... 600/590
(58) Field of Search ................................ 600/590, 587, 600/589; 340/870.16, 870.28; 433/69, 72; 455/100; 73/379.02, 862.626, 862.636

(56) References Cited

U.S. PATENT DOCUMENTS

| | | | |
|---|---|---|---|
| 3,094,115 A | 6/1963 | Polin | 128/2.1 |
| 3,297,021 A | 1/1967 | Davis et al. | 128/2 |
| 4,470,810 A | 9/1984 | Bourdeau et al. | 433/72 |
| 4,649,933 A | 3/1987 | Jackson | 128/774 |
| 4,688,580 A | 8/1987 | Ko et al. | 128/734 |
| 4,754,763 A | 7/1988 | Doemland | 128/739 |
| 4,764,114 A | 8/1988 | Jeffcoat et al. | 433/72 |
| 4,811,373 A | 3/1989 | Stein | 378/54 |
| 4,821,423 A | 4/1989 | Adams | 33/366 |
| 4,881,552 A | 11/1989 | Heyman | 128/774 |
| 4,991,301 A | 2/1991 | Hore | 33/366 |
| 5,024,239 A | 6/1991 | Rosenstein | 128/774 |
| 5,456,013 A | 10/1995 | Elias | 33/366 |
| 5,518,008 A | 5/1996 | Cucchiaro et al. | 128/777 |
| 5,632,093 A | 5/1997 | Elias | 33/366 |
| 5,680,874 A | 10/1997 | Takuno | 128/777 |

*Primary Examiner*—Max F. Hindenburg
*Assistant Examiner*—Brian Szmal
(74) *Attorney, Agent, or Firm*—Gifford, Krass, Groh, Sprinkle, Anderson & Citkowski, P.C.

(57) ABSTRACT

A device is provided for measuring the mechanical impedance of its surroundings. The device includes a force generator, a force sensor (32), an accelerometer unit (34), an electronic unit capable of calculating the impedance of the basis of outputs received from a device component and suitable power and control signal sources.

24 Claims, 3 Drawing Sheets

IMPLANTABLE MECHANICAL FORCE SENSOR

This application is a 371 of PCT/US00/26891 filed Sep. 29, 2000, which claims benefit of Ser. No. 60/157,189 filed Sep. 30, 1999.

TECHNICAL FIELD

The present invention generally relates to a sensing instrument to evaluate a mechanical force. More particularly, the present invention relates to a micro-sensing device which can be utilized in biological and non-biological applications to infer local stiffness and other dynamic parameters, for example, measurement of mechanical impedance and/or variation of impedance with time or other conditions, from which, for example, the state of osseointegration of a dental implant may be deduced.

BACKGROUND OF THE INVENTION

Optimal treatment using Branemark-style endosseous dental implants requires that the implant be stably osseointegrated before it is loaded. Research has shown that measurements of mechanical impedance can be used to infer the general state of osseointegration. However, to date, the accomplishment of such a measurement requires that the implant be surgically exposed before it can be tested utilizing a hand-held probe. Examples of prior art devices for measuring the osseointegration of bones are well known in the art. Particular examples include U.S. Pat. No. 5,024,239 to Rosenstein which discloses an apparatus for detecting loosening of an implant embedded in a bone of a limb of a patient. The disclosed apparatus includes a vibrator which is pressed into engagement with a limb to impart a vibratory motion to the bone which is received by a pickup device which is pressed into engagement with the limb a distance from the vibrator wherein the output signal transmitted through the bone implant is analyzed in order to measure the amount of implant fixation. However, the Rosenstein '239 patent does not disclose an implantable or partially implantable apparatus.

U.S. Pat. No. 5,518,008 to Cucchiaro et al. discloses a dental analyzer for analyzing dental implants which includes a dental probe which is placed in contact with a patient's dental implant. A force is applied to the dental implant through a hammer fired by an actuator disposed in the probe which impacts the dental implant and vibrates the dental implant. An accelerometer, disposed within the probe, measures the acceleration time history of the vibrating implant and a processor converts the measured acceleration time history into a measurement indicative to the condition of the dental implant. However, the Cucchiaro et al. '008 patent does not disclose an implantable or partially implantable device which is utilized to assess the mechanical impedance of the surrounding physical structures including human or animal tissues.

U.S. Pat. No. 4,754,763 to Doemland discloses a non-invasive method of testing the integrity of an in vivo bone and an apparatus for performing the method which includes placing an electrical vibration transducer against the exterior of the soft tissue surrounding the bone and generating a mechanical vibration in the bone by striking the bone with a reflex hammer. The signal received by the vibration transducer is converted into a measurement of the integrity of the bone. However, the Doemland '763 patent does not disclose an implantable or partially implantable device for measuring the mechanical impedance of physical structures.

All of the prior art devices for either sensing and measuring the degree of osseointegration or the measurement of local stiffness utilize external probes. It would be preferable and desirable if a clinician could evaluate the degree of osseointegration in a non-invasive manner, exposing the implant only when it is demonstrably stable enough for loading. Additionally, it would be further desirable and advantageous to have a micro-sensing device whose primary sensing components are small enough that they can be temporarily or permanently implanted, for example, as a component of a dental implant. Further, a device embodying this invention also has utility to temporarily or permanently be emplaced within non-living materials or structures whose condition or integrity could thereby be nondestructively monitored on the basis of local mechanical impedance.

SUMMARY OF THE INVENTION

A dynamic sensing device includes a force generator, an accelerometer unit, an electronic unit, a power source and a control signal source. The electronic unit calculates a force measurement from an output received from the force generator or accelerometer unit. The dynamic sensing device is sufficiently small as to be implantable within a mechanical structure or biological tissue. A force sensor is also included when the force generator does not yield a force with a known time profile.

An implant according to the present invention includes a housing having a cavity therein, a closure adapted to selectively engage the cavity of the implant housing, and a force sensing device as detailed above. The use of an implanted device to produce a force independent of a preload bias in order to measure impedance of an implant is also disclosed.

A process is disclosed for applying a known force at the boundary between the device and a structure to be characterized, without a concomitant preload bias. By sensing the acceleration of a secondary mass elastically mounted to the device, the acceleration of the device is readily calculated. By a mathematical combination of the applied force and resultant acceleration, it is possible to determine the impedance of the structure to be characterized, which impedance is often a parameter of diagnostic interest.

DETAILED DESCRIPTION OF THE INVENTION

Figure 1:
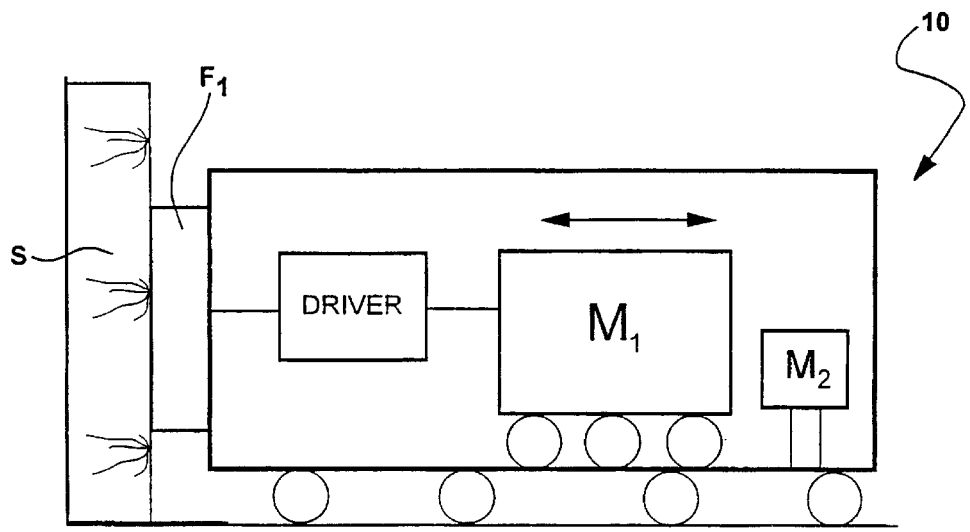
FIG. 1 is a schematic diagram of an implantable excitation and sensing subsystem according to the present invention.

The subject invention generally encompasses an apparatus which can be, at least in part, implanted within a larger structure illustratively including structural materials, human or animal tissues, either temporarily or permanently, to assess the local mechanical impedance of a physical structure, such as a medical implant, by causing the apparatus to vibrate or otherwise exert a known or measurable force upon its surroundings, measuring the resulting motion of the apparatus, and inferring the mechanical impedance of the surrounding structures in order to assess certain characteristics of those structures. In a particular embodiment of the subject application, the subject invention can comprise a plurality of miniature motors, force sensors, and accelerometers produced either by conventional or microelectromechanical (MEMS) techniques.

The subject invention has applications in various fields and can include the measurement of the progressive osseointegration of dental implants when the implants are otherwise inaccessible for measurement; measurement of the integrity of other implanted devices, particularly those having an interface with bone, e.g. hip replacements, bone anchors, etc.; the measurement of instantaneous tension or tone of individual muscle bundles, tendons, or regions of tissue, for purposes including the management or the correction of neuromuscular deficiencies; the noninvasive, inferential determination of the tension in engineering structures, illustratively including cables, shells, tanks, and other flexible elements whose transverse impedance varies with tension; and determination of the instantaneous condition or progressive change in the mechanical integrity of materials and structures including metals, glass, crystalline substances, polycrystalline substances, polymers, adhesives, cement, concrete, fiberglass, dispersed composites, adhesively bonded joints, and fastener structures such as rivets, bolts re-bar and the like.

In the most general terms, the complex mechanical driving-point impedance of a supporting structure is sensed. For the purposes of the present invention, the use of following equation uses the force-velocity energy pair, whence:

$$Z = F/V | \text{fundamental component, preload } F_o, \text{ frequency } \omega_o,$$

a complex quantity. The conditions are important for non-linear analyses.

Consider first an embodiment of the present invention operative as an implant sensor. It has been determined that, for transverse loading at moderate acoustical frequencies (2–5 kHz), a conventional implant can be adequately modeled as a first-order linearized dynamic system including one spring K, one mass M, and one viscous damper C. Constraining M to be the total mass of the implant, stiffness has been measured on the order of $2 \times 10^6$ N/m; while the effective stiffness obviously depends on the point of application, only the rigid body mode is significant. A resonance in the range of 2 to 4 kHz is normal.

While previous work has demonstrated that the effective stiffness K and other dynamic parameters may vary with an applied preload, a major aspect of the present invention is that it produces precisely characterized low-amplitude forces typically of between 1 to 1000 milli-Newtons without any preload bias, and therefore is not subject to nonlinear effects which render measurements made with external probes difficult to interpret.

The implantable subsystem 10 includes excitation and sensing components. FIG. 1 is a schematic diagram of this subsystem. A primary mass $M_1$ is driven to act as a force generator so as to generate a reaction force $F_1$ at the boundary of the device with a sampling structure, S. The value of this force can be either sensed by resistance or piezoelectric means or inferred accurately from known device properties. The resulting device acceleration is sensed from the motion of a second, elastically supported mass $m_2$, where preferably $m_2 \ll M_1$, defined herein as an accelerometer. The primary mass can be driven in any of a variety of ways illustratively including capacitive, piezoelectric, magnetic, or as an eccentric shaft load. The primary mass need not move in a periodic fashion, provided that the force which it imparts to its environment is accurately inferred as a function of time. Therefore, aperiodic forcing functions such as impulses can be used, as can forces resulting from natural environmental forces illustratively including those due to chewing or walking or normal structural motion. Preferably, the driving frequency ($\omega_d$) is variable over a relatively wide range of acoustic frequencies; however, the device could be used to obtain valid data even if it were necessary to use a tuned single frequency system. If possible, these measurements should be made simultaneously on two or even three orthogonal axes.

While the primary purpose and function of the instrument is to measure impedance, it would also be desirable and advantageous to have the capability to measure static or quasi-static loads across the package. There are many research applications requiring measurements of forces within bone and other tissues, and present instrumentation is inadequate for this purpose.

Figure 2:
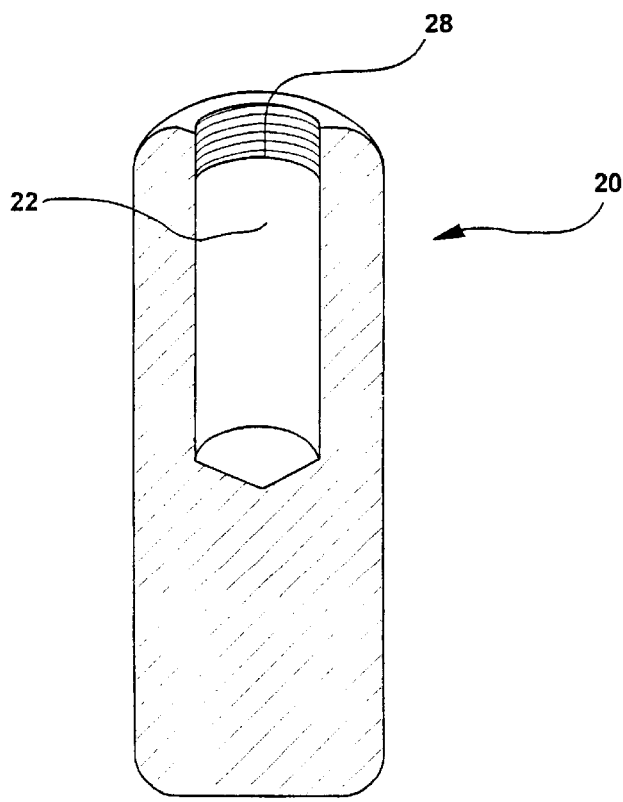
FIG. 2 is a side cut-away view illustrating typical dimensions of an implant according to the present invention.

For the present application in a preferred embodiment, the sensor package is embedded in the healing cap which is left screwed tightly into the dental implant during the healing period. This healing cap may be metallic or polymeric material illustratively including polyamides, polyesters, polyalkylenes, DELRIN (GE), fluoropolymers, such as TEFLON (DuPont) and PTFE. The use of a non-metallic cap may be preferable for several reasons: ease of embedment, access for wires, and the possibility of electromagnetic coupling for signal and/or power. FIG. 2 shows the dimensions of a typical implant 20. The implant 20 is generally cylindrical and has a cavity 22 therein. The cavity 22 is adapted to receive a complementary closure (not shown). Preferably, the cavity 22 has threads 24 designed to enmesh complementary threads of a closure. It is appreciated that different shapes and relative positions of a cavity are operative for an implant as dictated by the specifics of the installation as known to one skilled in the art. For many applications, the sensor package should be smaller than 1 mm in at least two dimensions, although for other applications, a larger sensor package is contemplated.

Figure 3:
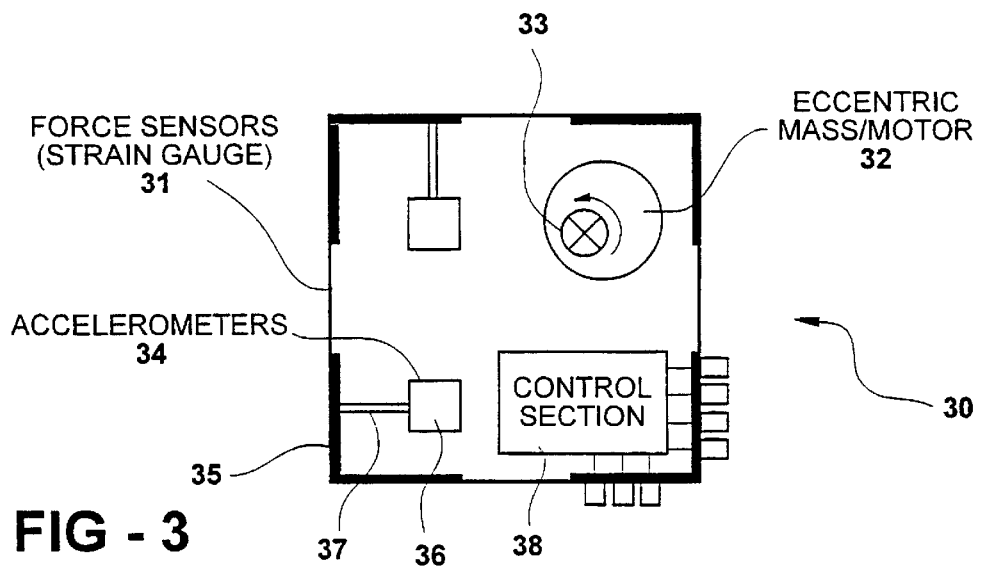
FIG. 3 is a schematic diagram illustrating a further embodiment of a possible two-axis package.

FIG. 3 illustrates a further embodiment of a possible two-axis package at 30. At least one force sensor 32 is located at a boundary interface between the package 30 and the surrounding structure S. The force sensor 32 according to the present invention illustratively includes a load cell, a strain gage or a variable resistor. It is appreciated that a force sensor is not needed in those embodiments in which the force time profile is known through calculation or previous measurement. Preferably, an amplifier is also provided to enhance load cell signal output. Preferably, at least two force sensors are provided within a package 30 at an angled orientation relative to one another in order to provide multiple axis sensor output. Preferably, the at least two sensors are positioned approximately orthogonal to one another. It is appreciated that multiple force sensors within a package 30 optionally include multiple types of force sensors within the same package 30. The at least one force sensor 32 measures forces generated by the rotation of an eccentric mass 34 about a drive shaft 36. As detailed with respect to FIG. 1, it is appreciated that the movement of the primary mass can be driven in a variety of other ways illustratively including capacitive, piezoelectric and magnetic. At least one accelerometer 34 is affixed to package housing 35 for each force sensor 31 present within the package 30. The accelerometer 34 includes a mass 33 coupled to the housing 35 by way of an elastic connector 37.

Preferably, the eccentric mass 32 is considerably greater than elastically supported mass 36. Preferably, each of the accelerometers 34 is oriented angularly from one another in a manner corresponding to the orientation between force sensors 31. A control section 38 is affixed to the housing 35 to provide operational control of the eccentric mass 32 and collect data from the at least one force sensor 31 and at least one accelerometer 34. It is appreciated that an energy source for a sensor package 30 is provided within the housing 35 by a battery unit or provided externally through conduction wires or wireless power transfer devices known to one skilled in the art. The package housing 35 being adapted to be secured to a surrounding structure and/or be inserted within the bore of an implant.

Figure 4:
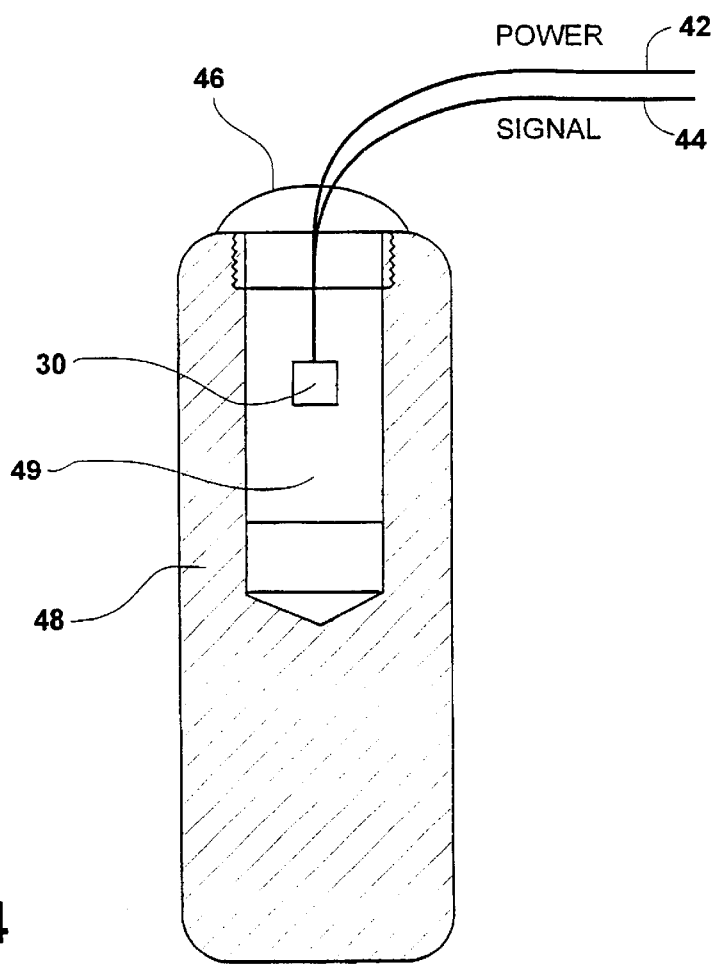
FIG. 4 is a side cut-away view illustrating sensor package encapsulation in a healing cap and an implant of FIG. 2.

FIG. 4 illustrates how a sensor package, such as 30 shown in FIG. 3, is encapsulated within an implant having a healing closure. A sensor package 30' having an external power lead 42 and an external signal communication lead 44 coupled thereto are fed through a healing closure 46 selectively engaging an implant 48 through complementary threads. The sensor package 30' being suspended within the bore 49 of the implant 48. It is appreciated that the bore 49 is optionally filled with a space filling substance of high mechanical impedance in order to facilitate force propagation to the implant 48. A configuration as depicted in FIG. 4 with external leads is recognized to have particular utility in laboratory and research settings.

Figure 5:
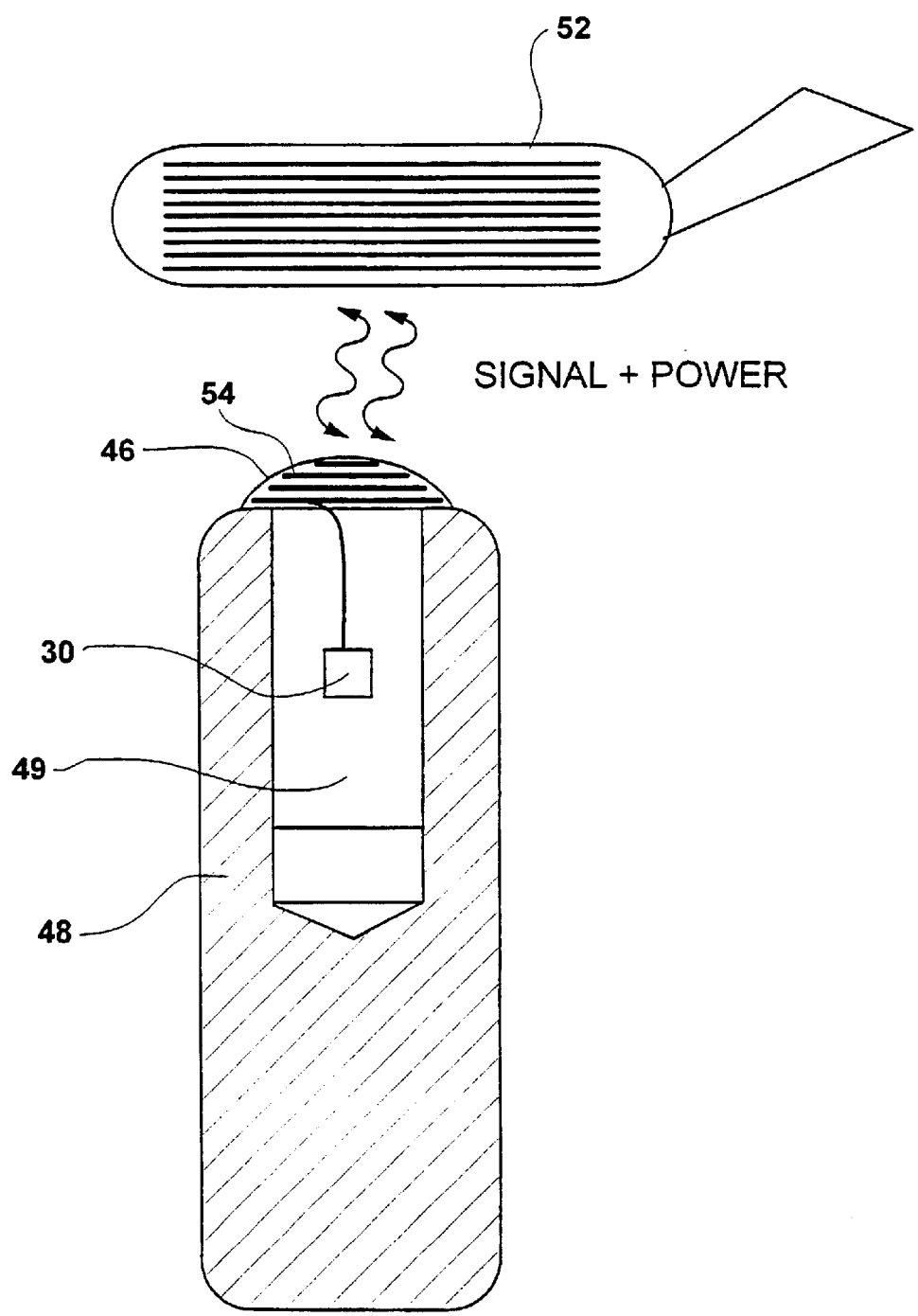
FIG. 5 is a side cut-away view showing a wireless implantable device according to the present invention adapted to be implanted with a dental implant.

FIG. 5 shows a wireless implantable version wherein the device is adapted to be implanted with a dental implant and then be externally powered and/or stimulated to generate impedance measurements which can be converted into measurements of osseointegration of the implant and wirelessly or non-wirelessly transmitted to a receiver. The numbers designating aspects of FIG. 5 that correspond to numbers used with respect to FIG. 4 are intended to have like meanings. The wireless power and data communication utilizes conventional wireless technology illustratively including microwave, RF and infrared energies to communicate between the sensor package 30' and an external transponder 52. The transponder 52 in communication with the sensor package 30' by way of a transponder antenna 54 coupled to the sensor package 30'.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

What is claimed is:

1. A dynamic implanted sensing device, said device comprising:
   an implanted force generator producing a known force time profile;
   an implanted accelerometer unit;
   an electronic unit calculating a dynamic force measurement from an output received from a device component selected from the group consisting of: said force generator and said accelerometer; and
   a power source and a control signal source.

2. The device of claim 1 wherein the known force time profile is determined with a force sensor.

3. The device of claim 1 wherein the known force time profile is obtained from inertial properties of said force generator.

4. The device of claim 1 wherein the dynamic force measurement is transmitted by a wireless transmitter to a transducer external to said device.

5. The device of claim 1 wherein the dynamic force measurement is impedance.

6. The device of claim 1 wherein said power source is external to said device.

7. The device of claim 1 wherein at least one of the device components selected from the group consisting of: said force generator, said force sensor, and said accelerometer, is a MEMS fabricant.

8. An implant comprising:
   an implant housing having a cavity therein;
   a closure adapted to selectively engage the cavity of said implant housing; and
   a dynamic sensing device according to claim 1 adapted to insert within the cavity.

9. The implant of claim 8 wherein said closure further comprising a wireless communication antenna.

10. A dynamic implanted sensing device, said device comprising:
    an implanted force generator producing a known force time profile;
    an implanted accelerometer unit;
    an electronic unit calculating a dynamic force measurement from an output received from a device component selected from the group consisting of: said force generator and said accelerometer; and
    a power source and a control signal source;
    wherein the output of said device is employed to infer the state of a non-biological adjacent structure.

11. The device of claim 10 wherein the non-biological adjacent structure is an engineering material selected from the group consisting of: metals, glass, crystalline substances, polycrystalline substances, polymers, adhesives, cement, concrete, fiberglass, dispersed composite, laid composite, and fastener structures.

12. A process for force measurement comprising the steps of:
    producing a force independent of a preload bias at a device-sampling structure boundary;
    sensing acceleration by measuring the relative displacement of a secondary mass elastically mounted to said device; and
    calculating impedance therefrom.

13. The process of claim 12 further comprising the step of relating the force measurement to sampling structure integrity wherein the sampling structure is selected from a group consisting of bone, dental tissue, cable, a shell, a storage tank, composite materials, adhesively bonded joints, welds and fasteners.

14. The process of claim 12 wherein producing a force independent of a preload bias occurs through a test force provided by an external environmental condition.

15. The process of claim 14 wherein the external environmental condition arises through ordinary sampling structure operation.

16. The process of claim 14 wherein the test force is provided by external artificially applied force at the time of sensing.

17. A dynamic implanted sensing device, said device comprising:

a plurality of implanted force sensors;

an implanted force generator producing a known force time profile, wherein the known force time profile is determined with a force sensor;

a plurality of implanted accelerometer units configured to provide a force measurement in two axes;

an electronic unit calculating a dynamic force measurement from an output received from a device component selected from the group consisting of: said force generator and said accelerometer; and a power source and a control signal source.

18. A dynamic implanted sensing device, said device comprising:

a force generator producing a known force time profile;

an accelerometer unit;

an electronic unit calculating a dynamic force measurement from an output received from a device component selected from the group consisting of: said force generator and said accelerometer; and a power source and a control signal source, wherein the device is implanted within biological tissue.

19. The device of claim 17 wherein said dynamic sensing device infers the state of integration of an implant into bone.

20. The device of claim 19 wherein said implanted dynamic sensing device is affixed to a dental implant.

21. The device of claim 20 wherein said implanted dynamic sensing device measures integration status.

22. An implant comprising:

an implant housing having a cavity therein;

a closure adapted to selectively engage the cavity of said implant housing; and a dynamic sensing device comprising a force generator producing a known force time profile; an accelerometer unit; an electronic unit calculating a dynamic force measurement from an output received from a device component selected from the group consisting of: said force generator and said accelerometer; and a power source and a control signal source, said dynamic sensing device adapted to insert within the cavity, wherein leads extend from said dynamic sensing device through said closure.

23. An implant comprising:

an implant housing having a cavity therein;

a closure adapted to selectively engage the cavity of said implant housing; and a dynamic sensing device comprising a force generator producing a known force time profile; an accelerometer unit; an electronic unit calculating a dynamic force measurement from an output received from a device component selected from the group consisting of: said force generator and said accelerometer; and a power source and a control signal source, said dynamic sensing device adapted to insert within the cavity, wherein said dynamic sensing device calculates two axes impedance measurements.

24. An implant comprising:

an implant housing having a cavity therein;

a closure adapted to selectively engage the cavity of said implant housing; and a dynamic sensing device comprising a force generator producing a known force time profile; an accelerometer unit; an electronic unit calculating a dynamic force measurement from an output received from a device component selected from the group consisting of: said force generator and said accelerometer; and a power source and a control signal source, said dynamic sensing device adapted to insert within the cavity, wherein a force is generated within said device independent of a preload bias.

* * * * *

UNITED STATES PATENT AND TRADEMARK OFFICE
CERTIFICATE OF CORRECTION

PATENT NO. : 6,712,778 B1
DATED : March 30, 2004
INVENTOR(S) : Robert Lee Jeffcoat and Lance C. Ramp It is certified that error appears in the above-identified patent and that said Letters Patent is hereby corrected as shown below:

Column 7,
Line 23, replace "17" with -- 18 --.

Signed and Sealed this

First Day of February, 2005

JON W. DUDAS
*Director of the United States Patent and Trademark Office*